United States Patent [19]

Peterson

[11] 4,015,599

[45] Apr. 5, 1977

[54] ANESTHETIC DELIVERY SYSTEM

[75] Inventor: Laurence I. Peterson, Doylestown, Pa.

[73] Assignee: Rohm and Haas Company, Philadelphia, Pa.

[22] Filed: July 21, 1975

[21] Appl. No.: 597,810

[52] U.S. Cl. .......................... 128/188; 260/2.1 R; 261/DIG. 65

[51] Int. Cl.² ........................................ A61M 16/00

[58] Field of Search .................. 128/188, 187, 192; 261/94, 95, DIG. 65, 142; 260/2.1 R, 2.1 E, 211.5 R, 2.5 R, 2.5 HB; 424/79 R

[56] References Cited

UNITED STATES PATENTS

| | | | |
|---|---|---|---|
| 2,549,593 | 4/1951 | Gardenier | 128/188 |
| 3,531,463 | 9/1970 | Gustafson | 260/211.5 R |
| 3,592,191 | 7/1971 | Jackson | 128/188 |
| 3,627,708 | 12/1971 | Morse et al. | 260/2.1 E |
| 3,665,073 | 5/1972 | Marshall et al. | 424/79 |
| 3,843,566 | 10/1974 | Barrett | 260/2.1 E |

*Primary Examiner*—Robert W. Michell
*Assistant Examiner*—Henry J. Recla

[57] ABSTRACT

Improved system for delivering a controllable concentration of anesthetic gas to a patient by eluting with a carrier gas a solid polymeric adsorbent previously loaded with an anesthetic, the concentration being dependent only on the adsorbent temperature and the initial quantity of adsorbed anesthetic. Preferred embodiments utilize the polymeric adsorbent's capability of delivering a broad range of concentrations at low flow rates in a recycle delivery system.

7 Claims, No Drawings

ANESTHETIC DELIVERY SYSTEM

BACKGROUND OF INVENTION

This invention is concerned with a system for delivering anesthetics and analgesics. More particularly, the invention is concerned with a method for delivering anesthetic and analgesic inhalation gases. When used in a broad sense hereinafter and in the claims, "anesthetic" is intended to include the administration of inhalation gases which are both anesthetic and/or analgesic.

Present delivery systems for inhalation anesthetics utilize the principle that a volatile liquid maintains a constant vapor pressure in the gas phase above the liquid. Anesthesia machines are constructed so that a stream of carrier gas passes through a baffled mixing chamber containing a few hundred milliliters of the liquid anesthetic. This stream becomes saturated with anesthetic vapors and the concentration is determined exclusively by the temperature (the higher the temperature, the higher the anesthetic concentration in the saturated vapors). The saturated stream is then mixed with a controlled amount of oxygen and/or nitrous oxide to dilute the saturated stream to a known concentration which is then delivered to the patient. The anesthesiologist determines the concentration from the temperature and by adjustment of a complex series of valves and flow meters.

Since each anesthetic has a different vapor pressure, a recalibration or even replacement of the vaporizer is necessary each time the anesthetic is changed.

Anesthetic concentrations of 0.5 – 4% are generally employed. Recommended flow rates for proper functioning of the equipment are in the 2 – 4 liters/min range. However, flow rates of 1000 cc/min are more desirable since this is the rate of oxygen uptake by the patient. The reduction of flow rates from 2 – 4 liters/min to 200 – 400 cc/min is commonly accomplished by a pop-off valve usually located on a surge or breathing bag.

The present methods of delivering inhalation anesthetics possess a number of substantial drawbacks (some of them inherent) which although recognized by the large majority of anesthesiologists have heretofore not been resolved in a satisfactory manner. These disadvantages include the inability of present metering devices, particularly in recycling systems, to effectively provide desired concentrations of anesthetics at less than 2 liters/min. flow rates. As mentioned hereinbefore the decrease in flow rates is typically effected by a pop-off valve. Unfortunately pop-off valves commonly release the anesthesia into the operating room itself, which is further disadvantageous since it may cause the operating surgeon to become drowsy at times when full concentration is absolutely essential. It is also suspected that prolonged exposure of operating personnel to anesthetics such as halogenated ethane may give rise to kidney and liver problems. Additionally, there has been alleged a relationship between exposure to inhalation of anesthetics and the high statistical rate of miscarriages experienced by operating room nurses. Venting inside and outside the operating room has been known to contaminate the closed circulatory air system of hospitals causing air pollution within the hospital. Regardless however of where the anesthesia is vented, excessive flow rates which require venting cause a considerable waste since up to 90% of the anesthetic gas delivered is unused.

A further difficulty arises when the exhaled gas is fed back via a closed recycling system eventually into the surge or breathing bag. The in-put of gas containing an unknown concentration of unused anesthetic obviously impairs the anesthesiologists's ability to establish the influent concentration of anesthesia that the patient inhales. Although the experienced anesthesiologist carefully determines the unconscious state of the patient during an operation by monitoring the patient's vital signs such as heart beat, etc., it would obviously be of great assistance for him to know exactly what amount of anesthetic the patient inhales at any given time and just as importantly for him to possess the ability to control precisely the amount of anesthetic supplied to the patient.

A further drawback of today's complicated anesthesia machines is their high maintenance cost. They are usually scheduled weekly for cleaning and "degumming" of the mixing chamber and ancillary equipment. Conscientious anesthesiologists frequently feel obligated to personally perform this function. A system which obviates the cleaning would therefore result in considerable savings of valuable time.

Inhalation anesthetics are sometimes used outside of hospital operating rooms, such as for example in dentists' offices. Dentists frequently use local analgesics by injection although they would prefer inhalation analgesics were it not for the cost of today's complex anesthesia machines and the mechanical difficulty of supplying dilute concentrations of gas to achieve a low analgesic state in the patient. Halogenated anesthetics such as trichloroethylene and methoxyflurane which are generally preferred cannot be used as analgesics with most present day equipment since the extremely dilute concentrations which are all that is necessary are not obtainable due to these anesthetics' great volatility in the liquid form. Delivery of analgesics or anesthetics by inhalation would however be preferred, if possible, as it allows the patients quick and total recovery without withdrawal symptoms commonly associated with narcotics delivered by injection. An increased number of patients have developed allergies to "local" analgesics and would therefore be benefited by thegreater range available in inhalation analgesics. Such analgesics would further establish better patient rapport particularly among children by eliminating the fears associated with needle injections.

It will be apparent, therefore, that some of the difficult problems confronting medical personnel in administering inhalation narcotics have been those of accurately and reliably delivering specific concentrations of gas without waste or danger to operating personnel. While various mechanical expedients have been developed for reducing flow rates, safely venting excess anesthetic gas and regulating or monitoring equipment, none has been entirely satisfactory or adequate under all operating conditions. Hence, those concerned with the development and use of inhalation narcotic systems have recognized the need for relatively simple, safe, reliable and accurate system which will be economical in price as well as use.

A relatively uncomplicated method and apparatus for delivering gaseous anesthetics in a closed system of anesthesia has been previously disclosed in Moyat U.S. Pat. No. 3,183,906, issued May 18, 1965. By one embodiment of that method essentially pure anesthetic is introduced into a carrier gas from a "reversible physical absorbing agent" (activated carbon is given as a preferred type adsorbent) and delivered together with the carrier gas to the patient. In another aspect, the Moyat method involves a closed anesthesia system in which a patient's exhaled gas is recycled through the adsorbing agent containing the anesthetic, with the carbon dioxide exhaled by the patient being removed and fresh oxygen added to make up for that which was consumed.

Unfortunately, the Moyat method which appears to offer great advantages in economy, safety and simplicity compared to existing systems for delivering anesthetics, has not gained widespread acceptance. At least in part, this lack of acceptance may be due to the unsuitability of activated carbon for sustained and controllable release of adsorbed anesthetics. Both the capacity for adsorption of anesthetics and the delivery characteristics of activated carbon vary appreciably from batch to batch. Frequently the initial delivery rate of anesthetic from activated charcoal is greater under ambient temperatures than desirable for anesthesia, necessitating complicated control means to reduce concentration. The friable nature of charcoal, leading to the production of a fine charcoal dust, may also lead to problems of containment and possibly blockage of sensitive control devices.

I have now discovered that a particular class of polymeric materials have outstanding properties for the adsorption and retention of common anesthetics, and are capable of uniform release of such anesthetics in controllable amounts and concentrations. Accordingly, these polymeric materials furnish an improved means for the practical implementation of the prior art methods of delivering anesthetics from a solid adsorbent material.

One of the principal disadvantages of the prior art activated carbon in anesthetic delivery is the wide difference in adsorption capacity and release, between different batches and different particle size carbon. This phenomenon is illustrated in the following table wherein w/w % means the weight of anesthetic divided by the weight of adsorbent plus anesthetic times 100.

TABLE I

Batch Variations on Delivery from NUCHAR WVH
(33 w/w% Halothane adsorbed on Carbon)

| Sample Carbon | Initial Halothane Delivery conc. at 30° C. (in air) |
|---|---|
| 8 × 30 Mesh (No. 1) | 0.30 % |
| 8 × 3 Mesh (No. 2) | 0.62 |
| 6 × 16 Mesh | 0.22 |

The large difference in delivery of anesthetic between Samples 1 and 2 in Table I is not unusual, nor is it surprising that different size particles yield different delivery rates. Further, the high initial anesthetic delivery of Sample 2, at relatively low temperature, makes this material of dubious value for anesthetic delivery which commonly employs sustained delivery concentrations of about 0.5% in air.

In contrast to the variations in delivery of anesthetics from activated carbon, the polymeric adsorbents useful by the method of the present invention are relatively uniform in delivery capability from batch to batch and can be routinely produced by chemical synthesis with uniform capabilities. Those polymers which are suitable include macroreticular homopolymers and copolymers which will adsorb at least 1.0 w/w % of an inhalation anesthetic from a gas stream at 25° C and atmospheric pressure containing 0.5 v/v % inhalation anesthetic. Further, such polymeric adsorbents will deliver to an eluting gas stream under atmospheric pressure a concentration of 0.5 v/v % of anesthetic, at a temperature below that which will cause decomposition of the polymeric adsorbent or appreciable volatilization of extractables therefrom, when said adsorbent is initially loaded with at least 1.0 w/w % inhalation anesthetic.

The polymeric macroreticular resins suitable as adsorbents according to this invention include any of the well known prior art macroreticular resins useful for adsorption or ion exchange (see, e.g., U.S. Pat. No. 3,531,463 ). Among these are the crosslinked and uncrosslinked homopolymers and copolymers of styrene, vinyl toluene, vinyl benzyl chloride, ethyl vinyl benzene, acrylonitrile, vinyl pyridine, ethyl thioethyl acrylate, diacetone acrylamide, ethyl thioethyl methacrylate, butyl methacrylate, ethylacrylate, methyl methacrylate, hydroxyethyl methacrylate, hydroxypropyl methacrylate, dimethylaminoethyl methacrylate, dimethylaminopropyl methacrylate, dimethyl acrylamide, vinyl pyrrolidinone, 5-methyl-5-vinyl pyridine, 4-vinyl pyridine, and 2-vinyl pyridine.

Polyfunctional materials which are suitable for production of macroreticular polymeric adsorbents or which may serve as crosslinkers for the above monomers include divinyl benzene, trivinyl benzene, trimethylol propane trimethacrylate (X-980), trimethylol propane dimethyacrylate, penta eythritol tetramethacrylate, penta eythritol trimethacrylate, ethylene glycol dimethacrylate, propylene glycol dimethacrylate, and butylene glycol dimethacrylate. The methods of producing macroreticular resins by suspension polymerization are illustrated in U.S. Pat. Nos. 3,843,566; 3,531,463 and 3,663,467.

The macroreticular resins may also be functionalized, i.e., converted to ion exchange resins without appreciably diminishing their capacity for adsorption of the anesthetic material. Suitable functional ion exchange groups that may even enhance the capacity of the polymeric adsorbents include sulfonic, carboxylic, amine oxide, sulfoxide, sulfone, ketone and amides.

The preferred macroreticular resins useful in accordance with the invention are those produced containing a large surface area, i.e., approximately 100 – 900 $m^2/g$, such as the styrene or ethyl vinylbenzene divinylbenzene (DVB) resins in which the DVB crosslinker is present in an amount between about 20 – 100%. This class of resins is marketed commercially by Rohm and Haas Company under its Amberlite trademark and designated as XAD-1, XAD-2 and XAD-4. Other preferred macroreticular polymers are acrylic ester-based materials marketed under the designations XAD-7, 8 and 12.

With regard to the anesthetics which may be useful in carrying out the invention, it should be understood that any liquid or gaseous anesthetic may be satisfactory. Specific anesthetics which have exhibited great utility have included chloroform, ether and vinyl ether, cyclopropane, halothane, methoxyflurane, enflurane and trichloroethylene. Preferred anesthetics are halothane, methoxyflurane and enflurane. Halothane, which is marketed broadly under the trademark Fluothane (trademark of Ayerst Laboratories, Inc.) is by far the most widely used anesthetic comprising an estimated 81% of the total inhalation anesthetic market.

In practicing the method of invention it will be necessary to use an apparatus for delivering the anesthetic fluid having an inlet and an outlet conduit connected to a chamber, said chamber containing a solid adsorbent bed which is capable when loaded with anesthetic of releasing a controllable, substantially constant concentration of anesthetic into an eluting fluid passed through the inlet, the bed, and then the outlet conduits. The solid adsorbent is herein further defined as one that will hold the anesthetic primarily in a two-dimensional phase as opposed to the liquid or gaseous state and as distinguished thereby from a support such as a wick which will hold an imbibed fluid largely in the liquid phase.

The carrier case which is used to elute the loaded adsorbent may be air, or any mixture of gases which includes oxygen. Preferred carrier gases are mixtures of oxygen and nitrous oxide. The concentration of the anesthetic in the carrier gas, depending upon the course of the patient and the degree of narcosis desired, will range from 0.01 to 20% by volume.

A preferred embodiment of the method of the invention comprises the use of a solid adsorbent in combination with a recycling or rebreathing system. It was surprisingly discovered that if unused portions of anesthetics, after having by-passed the patient, were led on to the solid adsorbent, the concentration of the effluent narcotic was in no way affected by this input. Instead such a secondary input merely prolongs the lifetime of the loaded solid adsorbent.

Recycling unused anesthetic and the gas mixtures exhaled by the patient involve avoiding three major possibilities of contamination. First, one must ensure that all expired carbon dioxide must be removed to avoid build-up to a dangerous level. Second, all expired water must be removed to avoid condensation. Third, sanitation must be achieved in surgical cases to preclude transfer of contagious diseases.

The preferred embodiment of the invention therefore utilizes a recycling chamber which additionally includes an agent to remove carbon dioxide and water. A further refinement would include a disinfectant in instances where sanitation is of major concern.

Known agents for the removal of carbon dioxide and water include calcium hydroxide and calcium chloride respectively. Naturally water removal may be accomplished by any deliquescent. Carbon dioxide may also be removed by a weak base resin in the free base form. A further refinement comprises a chamber containing adsorbent in combination with the weak base resin in the free base form to remove carbon dioxide and a strong acid resin in the hydrogen form to remove water. Optionally combined or admixed therewith may be a germicide functioning as a disinfectant.

A desirable embodiment of the invention would utilize a chamber of adsorbent with or without additional resins in the form of a disposable canister.

In view of the close proximity of the adsorbents to patients, particular care should be taken that none of the adsorbents release a detrimental amount of volatile extractants. In the case of polymeric adsorbents, this is of particular importance. Unless the adsorbents are specifically treated, there remains the possibility that extractants such as styrene, divinylbenzene, benzene, toluene, xylene, ethyl benzene, dimers and higher polymers or styrene and divinylbenzene may be present in the gas delivered to the patient.

Synthetic polymeric adsorbents may be modified to become relatively free of detrimental volatile extractants by various techniques. These techniques may include:

1. high temperature treatment under vacuum;
2. high temperature treatment while subjected to a flow of inert gas;
3. soxhlet extraction with ethylene dichloride;
4. steam stripping.

For example, the use of technique No. 3 followed by technique No. 1 produces a product having less than one part per million volatile components at 170° C. Technique No. 3 will produce a polymeric adsorbent having an even smaller amount of volatile components.

Steam stripping includes passing steam through the resin in slurried or dry form at flow rates of 1 to 10,000 bed volumes per hour and at temperatures of 100° – 150° C. Typically, the steam stripping will take from one-half to four hours. Care should be taken not to exceed the maximum temperature which is determined by the thermal stability of each resin. Generally, at temperatures approaching the glass transition temperature of the resins, usually at temperatures greater than 150° C., the polymeric resins lose their structure.

Commonly used analytical techniques for determining the presence of volatile extractants include mass spectrometry and gas chromatography.

Further experiments are included to assist the skilled worker in the art and in no way are intended to be limiting to the broad concept of the invention.

A. Various possible adsorbents are evaluated by their capacity for holding narcotics. The experiments are performed utilizing 20 cc of adsorbent and loading thereon various well-known anesthetics under normal room temperature and atmospheric pressure. By weighing the adsorbent before and after, the capacity of the various adsorbents is determined, as shown in the following Table II.

B. To determine the relationship between the amount of initial loading of anesthetic and the elution concentration, various samples of adsorbent C and Pittsburgh Carbon were loaded with different amounts of three anesthetics. The following Table III shows that each narcotic has different elution characteristics with halothane being preferred.

TABLE II

| Adsorbent | Composition | Adsorbent Capacities for Inhalation Anesthetics | | | | |
|---|---|---|---|---|---|---|
| | | Surface area | Character | Halothane | Enflurane | Methoxyflurane |
| A | Styrene-DVB polymer | 100 m$^2$/g | non-polar | 6.25 w/w% | 4.45 w/w% | |
| B | Styrene-DVB polymer | 300 m$^2$/g | non-polar | 17 | | 23.6 w/w% |
| C | Styrene-DVB polymer | 780 m$^2$/g | non-polar | 26 | 19 | 47 |
| D | Acrylic ester polymer | 450 m$^2$/g | slightly polar | 21 | 23 | 27 |
| E | Acrylic ester polymer | 140 m$^2$/g | slightly polar | 20 | — | — |
| F | Amine oxide polymer | 22 m$^2$/g | very polar | 4.5 | 3.9 | — |
| G | Sulfonic acid polymer | 571 m$^2$/g | very polar | 15 | 17 | — |

TABLE II-continued

| Adsorbent | Composition | Adsorbent Capacities for Inhalation Anesthetics | | Halothane | Enflurane | Methoxyflurane |
|---|---|---|---|---|---|---|
| | | Surface area | Character | | | |
| H | Pittsburgh G W Active carbon | 1000 m²/g | non-polar | 28 | 25 | 30 |

Adsorbents A through G are all available from the Rohm and Haas Company, Philadelphia.

Table III

Initial Anesthetic Elution Concentrations at Various Sample Concentrations of Adsorbent C and Pittsburgh Carbon

| Sample Composition w/w% | Concentration in Effluent (Vol/Vol %) | | | |
|---|---|---|---|---|
| | Halothane | Enflurane | Methoxyflurane | Halothane on P. Carbon |
| 5 | 0.20% | 0.16% | | |
| 8 | 0.44 | 0.50 | | |
| 10 | 0.54 | 0.60 | | 0 |
| 12 | 0.69 | 0.76 | | |
| 15 | 1.28 | 1.30 | 0.12% | |
| 20 | 1.96 | 2.6 | 0.18 | 0.01% |
| 25 | 3.20 | | 0.22 | 0.05 |
| 27 | | | 0.84 | 0.20 |
| 32 | | | 1.20 | 0.44 |
| 35 | | | | 1.60 |
| 38 | | | | 4.1 |
| 47 | | | 2.17 | |

To determine the effect of additional input concentration on the output concentration, two adsorbent C samples were loaded with 15% weight and 10% weight concentrations of halothane and subsequently subjected to additional halothane input to simulate a recycling system. The following Table IV shows the output being unaffected by subsequent input of anesthetic.

To determine the effective life of an adsorbent the output concentration of a halothane-loaded adsorbent C was monitored. The results are shown in Table V. It should be noted that this is an accelerated test since normal flow rates are not 25 bed volumes per minute but are in the range of 1 to 20 bed volumes per minutes. Normal beds are envisioned to be in the range of 0.1 to 1 liter in volume. It is interesting to note that any flow rates that are desirable may be used.

One embodiment, although not necessarily preferred, utilizes a mere replacement of vaporizer with an adsorbent in the present system. Such an embodiment would provide a constant concentration at flow rates of 2-4 liters/min. and continue to use a pop-off valve adsorbent bed.

Table IV

Initial Output Concentration of Halothane from Adsorbent C with Different Additional Input Concentrations of Halothane Bed volume = 20 cc
Flow rate = 25 BV/min O₂
Temperature = 24.5° C.

| Composition w/w % halothane on Adsorbent C | input (%) | output (%) |
|---|---|---|
| 15 | 0 | 1.5 |
| | 1.0 | 1.5 |
| | 1.5 | 1.5 |
| | 13 | 1.5 |
| 10 | 0 | 1.0 |
| | 1.5 | 1.0 |
| | 13 | 1.0 |

TABLE V

Elution Characteristics of Halothane on Adsorbent C (23° C)

Bed Volume (BV) = 20 cc
Anesthetic Loading = 10 w/w%
Flow = 25 BV min O₂

| BV | v/v% Halothane in Effluent |
|---|---|
| 0 – 300 | .18 |
| 325 | .17 |
| 500 | .15 |
| 700 | .12 |
| 875 | .11 |
| 1050 | .08 |
| 1300 | .06 |

The ease with which the polymeric adsorbents may be utilized to maintain a constant output of halothane anesthetic is illustrated below in Tables VI (0.5 halothane) and VII (1.0 halothane). For comparison purposes a carbon control sample is included in each table. It is important to note that while Amberlite XAD-4 will release over half of its adsorbed anesthetic at a constant concentration of 0.5% (Table VI) when the temperature is increased only 9.5 C°, a ΔT of approximately 40 C° is needed to obtain an equivalent utilization of anesthetic from activated carbon. Of equal significance, the carbon had an initial release temperature quite high and, accordingly, a rather high temperature was needed to achieve release of a high proportion of the anesthetic (Table VI). At a constant concentration of 1.0% halothane, the ΔT required for release of anesthetic from carbon, when compared to Amberlite XAD-4, was again larger than might be desired (see Table VII).

Table VI

Temperature V. Utilization* to Maintain Constant 0.5% Halothane Output

| NUCHAR WVH 8 × 30 | | Styrene/DVB Copolymer (Amberlite XAD-4) | | Trimethylolpropane trimethacrylate (Amberlite XAD-7) | |
|---|---|---|---|---|---|
| Temp. | Utilization | Temp. | Utilization | Temp. | Utilization |
| 41° C | 1.4% | 38° C | 2.4% | 27° C | 1.5% |
| 42 | 2.3 | 39 | 11.9 | 29 | 13.3 |

Table VI-continued

Temperature V. Utilization* to Maintain Constant 0.5% Halothane Output

| NUCHAR WVH 8 × 30 | | Styrene/DVB Copolymer (Amberlite XAD-4) | | Trimethylolpropane trimethacrylate (Amberlite XAD-7) | |
|---|---|---|---|---|---|
| Temp. | Utilization | Temp. | Utilization | Temp. | Utilization |
| 44 | 8.2 | 40 | 14.2 | 30 | 14.7 |
| 45.5 | 12.7 | 40.5 | 19.0 | 32 | 20.6 |
| 46 | 13.6 | 41 | 26.1 | 33 | 22.1 |
| 48.5 | 16.4 | 42.5 | 35.6 | 36 | 26.5 |
| 49 | 18.2 | 43.5 | 40.3 | 40 | 32.4 |
| 50.5 | 21.4 | 46.5 | 47.4 | 44 | 36.8 |
| 51 | 22.7 | 47.5 | 52.1 | 47 | 42.7 |
| 54 | 24.1 | | | 53 | 56.0 |
| 57 | 27.3 | | | 57 | 63.3 |
| 59 | 30.9 | | | | |
| 62 | 35.9 | | | | |
| 63.5 | 37.3 | | | | |
| 64 | 37.7 | | | | |
| 66 | 38.6 | | | | |
| 68 | 40.0 | | | | |
| 69 | 40.9 | | | | |
| 71.5 | 43.6 | | | | |
| 72 | 44.6 | | | | |
| 74 | 45.5 | | | | |
| 76 | 48.2 | | | | |
| 79 | 50.9 | | | | |
| 82 | 53.6 | | | | |
| 84 | 55.0 | | | | |
| 85.5 | 56.8 | | | | |
| 87.5 | 58.2 | | | | |
| 92 | 61.4 | | | | |
| 94 | 63.6 | | | | |

*Utilization: The amount (weight) of halothane eluted divided by the total amount loaded on the adsorbent multriplied by 100.

Table VII

Temperature V. Utilization to Maintain Constant 1.0% Halothane Output

| NUCHAR WVH 8×30 | | Styrene/DVB Copolymer (Amberlate XAD-4) | |
|---|---|---|---|
| Temperature | Utilization | Temperature | Utilization |
| 42° C | 1.7% | 50° C | 5.1% |
| 43 | 2.5 | 51 | 30.6 |
| 44 | 6.7 | 52 | 40.7 |
| 45 | 13.4 | | |
| 47 | 16.8 | | |
| 48 | 18.4 | | |
| 52 | 21.8 | | |
| 53 | 24.3 | | |
| 56 | 27.7 | | |
| 57 | 28.5 | | |
| 62 | 34.4 | | |

The uniformity of polymeric adsorbents for adsorption of two popular anesthetics is illustrated below in Table VIII.

Table VIII

Batch Variations on Capacity * of Amberlite XAD-4

| Sample | Surface Area (m²/g) | Halothane Capacity [a] | Enflurane Capacity [b] |
|---|---|---|---|
| 1 | 748 | 32.4 w/w% | 25.7 w/w% |
| 2 | 717 | 33 | 24.2 |
| 3 | 740 | 32 | 27.9 |

*Capacity data presented is w/w% anesthetic to adsorbent at breakthrough.
[a] 13% halothane in $O_2$ at 25° C and atmospheric pressure influent.
[b] Influent conc. 8.8 v/v% enflurane in $O_2$ at 25° C and atmospheric pressure.

Normally, the macroreticular polymeric adsorbent is contained in a canister which contains a heating device suitable for maintaining the temperature of the polymeric adsorbent. By this means the flow of anesthetic can be controlled or maintained at the desired concentration in the carrier gas passing through the canister. Care must, of course, be exercised in maintaining the temperature of the polymeric adsorbent below that which will cause any volatilization of extractables from the polymer or decomposition. With essentially all of the polymeric adsorbents of the invention, essentially complete release of adsorbed anesthetic (80+% is achieved at moderate temperatures, i.e, between 10° C and 100° C, well below the temperatures at which polymers liberate extractables or decompose (100° C and ≧ 150° C, respectively).

I claim:

1. A method of delivering a flow of anesthetic gas to a patient at a controllable, substantially constant concentration of such anesthetic in a gaseous carrier stream which comprises contacting the gaseous carrier stream with a bed of solid macroreticular polymeric adsorbent having adsorbed thereon a sufficient amount of anesthetic to produce a partial pressure of anesthetic high enough to cause sustained release of the anesthetic to the gaseous carrier stream to result in a concentration of anesthetic in the gaseous carrier stream suitable for anesthesia, maintaining the temperature of the bed below that which would cause volatilization of a detrimental amount of any extractable portion of the macroreticular polymeric adsorbent or decomposition of the adsorbent, but high enough to effect the sustained release of the anesthetic.

2. The method of delivering a flow of anesthetic gas in accordance with claim 1 wherein the macroreticular polymeric adsorbent is a crosslinked styrene or ethyl vinyl-benzene divinylbenzene copolymer containing 20 – 100% divinylbenzene with the remainder styrene or ethyl vinylbenzene 3. The method of delivering a flow of anesthetic gas in accordance with claim 1 wherein the macroreticular polymeric adsorbent is trimethylol propane trimethacrylate.

4. The method of delivering a flow of anesthetic gas in accordance with claim 1 wherein the gaseous carrier stream consists essentially of oxygen, nitrous oxide or a mixture of oxygen and nitrous oxide.

5. The method of delivering a flow of anesthetic gas in accordance with claim 1 wherein the gaseous carrier stream containing the anesthetic is delivered to a patient, recycled together with the expired gases from the patient through a purification system to remove moisture and carbon dioxide, and redelivered to the patient after further contact with the adsorbent containing the anesthetic.

6. The method of claim 1 wherein the anesthetic is halothane.

7. The method of claim 1 wherein the anesthetic is enflurane.

* * * * *